(12) United States Patent
Stephens et al.

(10) Patent No.: US 9,867,751 B2
(45) Date of Patent: Jan. 16, 2018

(54) LIMB IRRIGATION PAN DEVICE

(71) Applicants: Shannon N. Stephens, La Quinta, CA (US); Brenda Samuels, La Quinta, CA (US)

(72) Inventors: Shannon N. Stephens, La Quinta, CA (US); Brenda Samuels, La Quinta, CA (US)

(*) Notice: Subject to any disclaimer, the term of this patent is extended or adjusted under 35 U.S.C. 154(b) by 387 days.

(21) Appl. No.: 14/279,414

(22) Filed: May 16, 2014

(65) Prior Publication Data
US 2015/0328393 A1 Nov. 19, 2015

(51) Int. Cl.
| | |
|---|---|
| *A61M 3/02* | (2006.01) |
| *A61G 13/12* | (2006.01) |
| *A61G 7/075* | (2006.01) |
| *A61G 13/10* | (2006.01) |
| *A61H 35/00* | (2006.01) |
| *A61G 7/00* | (2006.01) |

(52) U.S. Cl.
CPC ....... *A61G 13/1245* (2013.01); *A61G 7/0755* (2013.01); *A61G 13/102* (2013.01); *A61G 13/1235* (2013.01); *A61M 3/0287* (2013.01); *A61G 7/0005* (2013.01); *A61G 7/075* (2013.01); *A61G 13/127* (2013.01); *A61H 35/00* (2013.01); *A61H 35/006* (2013.01)

(58) Field of Classification Search
CPC .................. A61H 35/00; A61H 35/006; A61H 2035/004; A61G 7/075; A61G 7/0755; A61G 13/102; A61G 13/1205; A61G 13/1235; A61G 7/0005; A61M 3/0287

USPC ........ 4/621; 5/606, 620, 621, 623, 630, 646, 5/647
See application file for complete search history.

(56) References Cited

U.S. PATENT DOCUMENTS

| | | | | |
|---|---|---|---|---|
| 635,891 | A * | 10/1899 | Holberg | A61H 35/00 4/535 |
| 665,673 | A * | 1/1901 | Fraley | A61H 35/00 4/535 |
| 2,086,244 | A * | 7/1937 | Smith | B60N 2/4673 297/411.24 |
| 3,920,144 | A * | 11/1975 | Callen | B65D 25/02 220/533 |
| 4,055,863 | A * | 11/1977 | Duval | A61G 7/0005 4/567 |
| 4,243,214 | A | 1/1981 | LaRooka | |
| 5,228,150 | A * | 7/1993 | Parker | A61H 9/00 239/558 |
| 5,381,562 | A | 1/1995 | Holloway et al. | |

(Continued)

*Primary Examiner* — J. Casimer Jacyna
(74) *Attorney, Agent, or Firm* — Daniel M. Cohn; Howard M. Cohn

(57) ABSTRACT

A limb irrigation pan device collects and removes irrigation fluid and debris from a surgical field when a limb is irrigated. The device includes a frame having a pair of opposed ends and a pair of longitudinal sides extending between the opposed ends. Respective upper surfaces of each opposed end are concavely arcuate and an upper edge of the frame defines an open top of the frame. A base is coupled to the opposed ends and the longitudinal sides defining a well for collecting a fluid passed into the frame through the open top. A porous sling is coupled to the frame for passing the fluid through the sling to be collected in the well. A drain coupled to the frame is in fluid communication with the well wherein the drain drains the fluid from the well.

14 Claims, 5 Drawing Sheets

(56) References Cited

U.S. PATENT DOCUMENTS

| | | |
|---|---|---|
| 5,697,921 A | 12/1997 | Blair |
| 6,016,578 A | 1/2000 | Malouf |
| 6,609,257 B1 | 8/2003 | O'Geary |
| 7,736,348 B2 | 6/2010 | Booth et al. |
| D621,927 S | 8/2010 | Dominguez et al. |
| 7,785,303 B2 | 8/2010 | Tapadiya |
| 2001/0025389 A1* | 10/2001 | Kitamura ............ A61G 7/0005 4/538 |
| 2011/0011408 A1 | 1/2011 | Born |
| 2011/0225726 A1 | 9/2011 | Dominguez et al. |

\* cited by examiner

LIMB IRRIGATION PAN DEVICE

BACKGROUND OF THE DISCLOSURE

Field of the Disclosure

The disclosure relates to pan devices and more particularly pertains to a new pan device for collecting and removing irrigation fluid and debris from a surgical field when a limb is undergoing debridement and irrigation.

SUMMARY OF THE DISCLOSURE

An embodiment of the disclosure meets the needs presented above by generally comprising a frame having a pair of opposed ends and a pair of longitudinal sides extending between the opposed ends. Respective upper surfaces of each opposed end are concavely arcuate and an upper edge of the frame defines an open top of the frame. A base is coupled to the opposed ends and the longitudinal sides defining a well for collecting a fluid passed into the frame through the open top. A porous sling is coupled to the frame for passing the fluid through the sling to be collected in the well. A drain coupled to the frame is in fluid communication with the well wherein the drain drains the fluid from the well.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
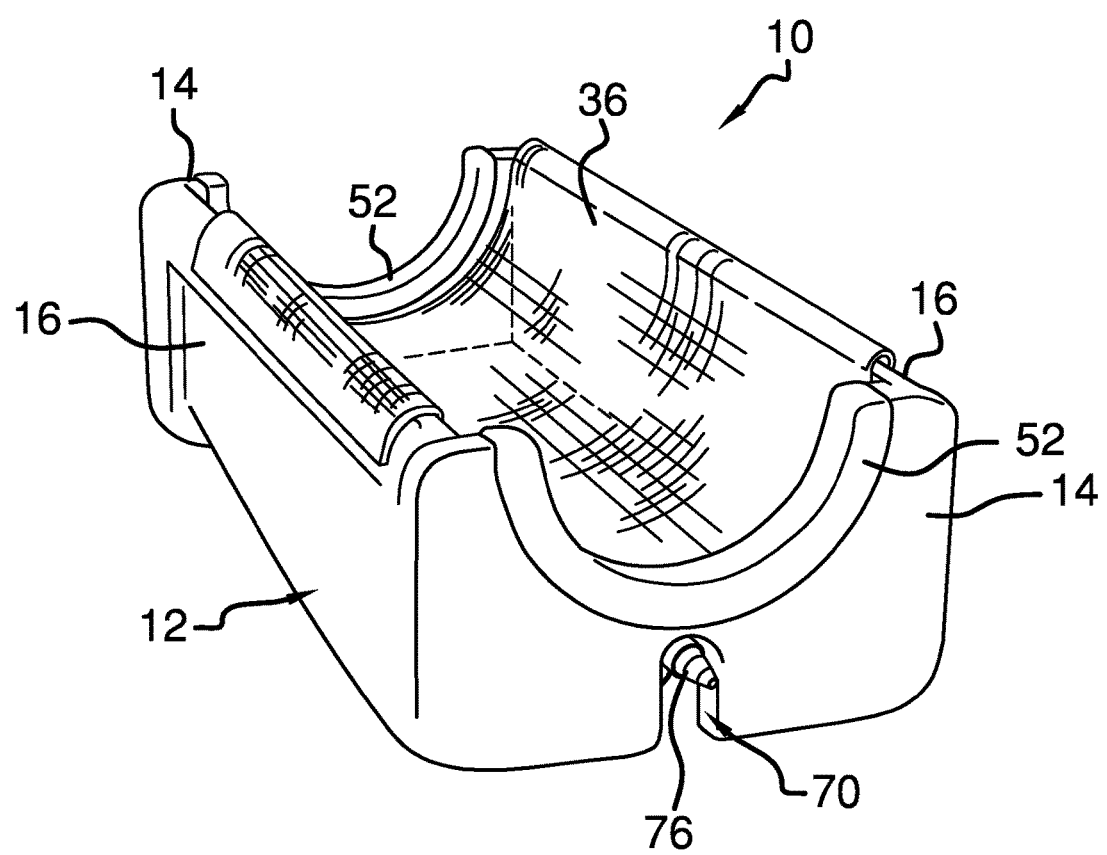
FIG. 1 is a top front side perspective view of a limb irrigation pan device according to an embodiment of the disclosure.
Figure 2:
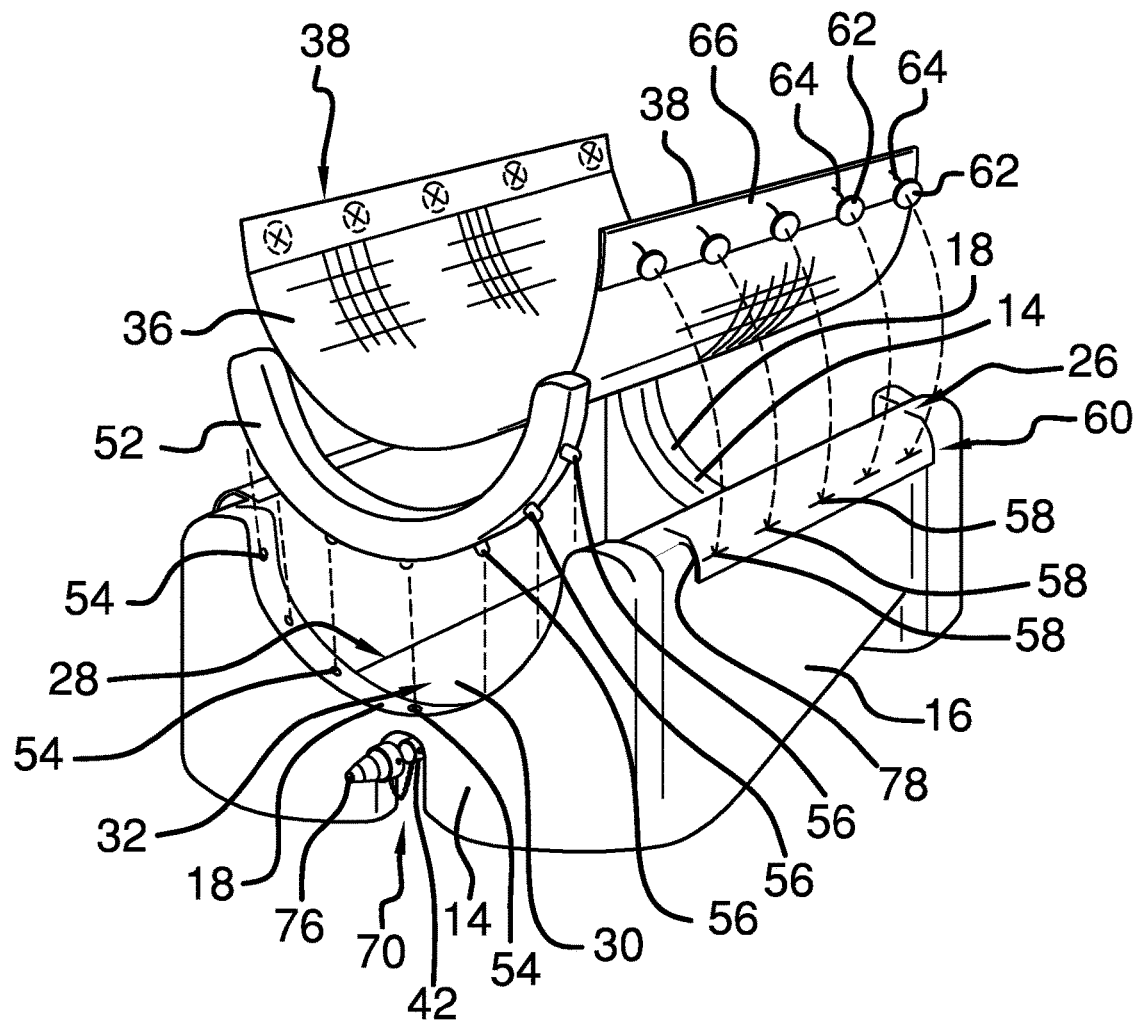
FIG. 2 is a partially exploded top front side perspective view of an embodiment of the disclosure.
Figure 3:
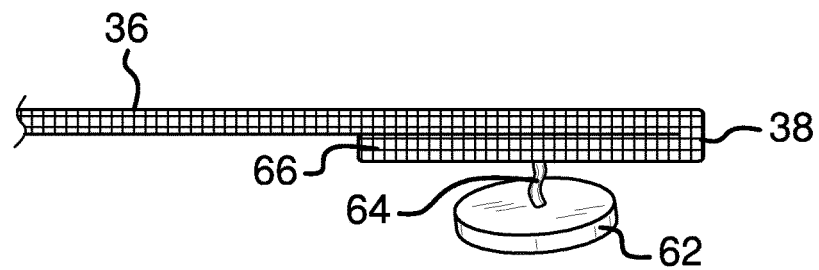
FIG. 3 is a detailed side view of an embodiment of the disclosure.
Figure 4:
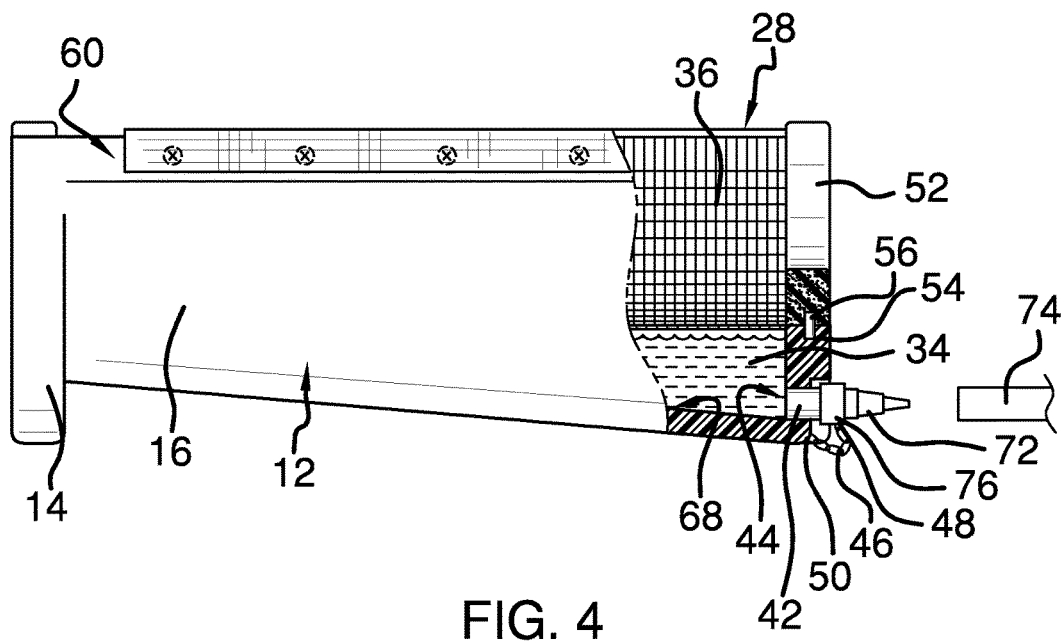
FIG. 4 is a partial cut-away side view of an embodiment of the disclosure.
Figure 5:
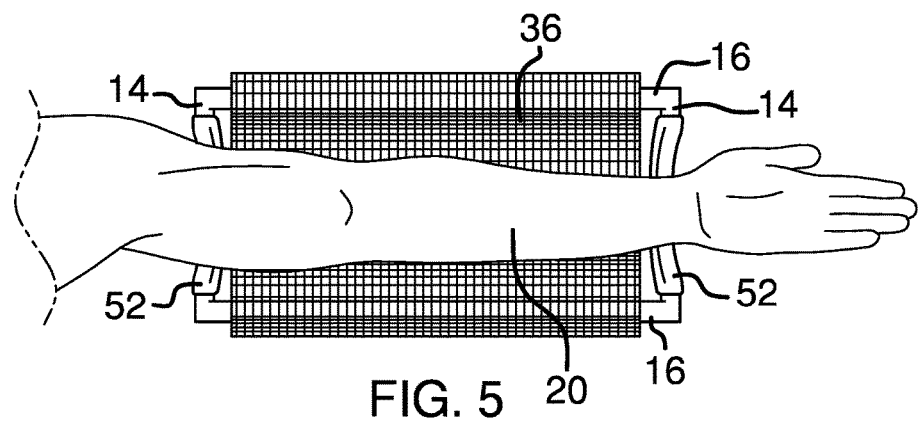
FIG. 5 is a top view of an embodiment of the disclosure in use.
Figure 6:
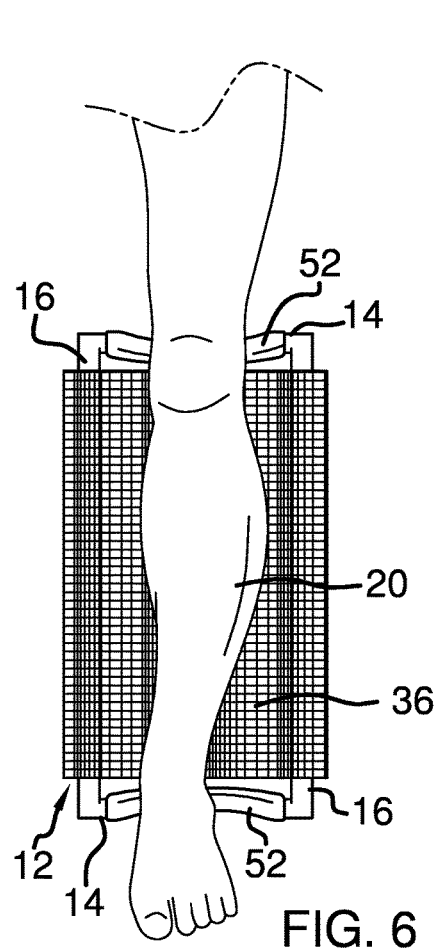
FIG. 6 is a top view of an embodiment of the disclosure in use.
Figure 7:
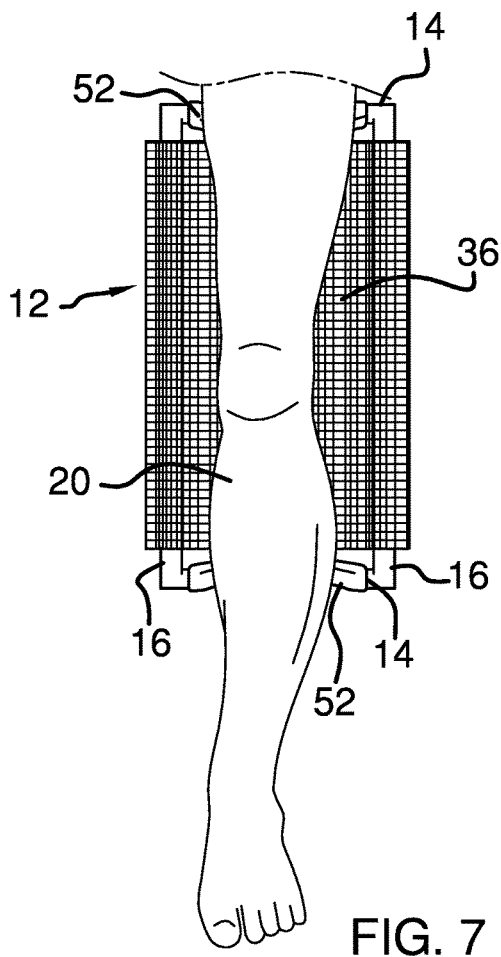
FIG. 7 is a top view of an embodiment of the disclosure in use.
Figure 8:
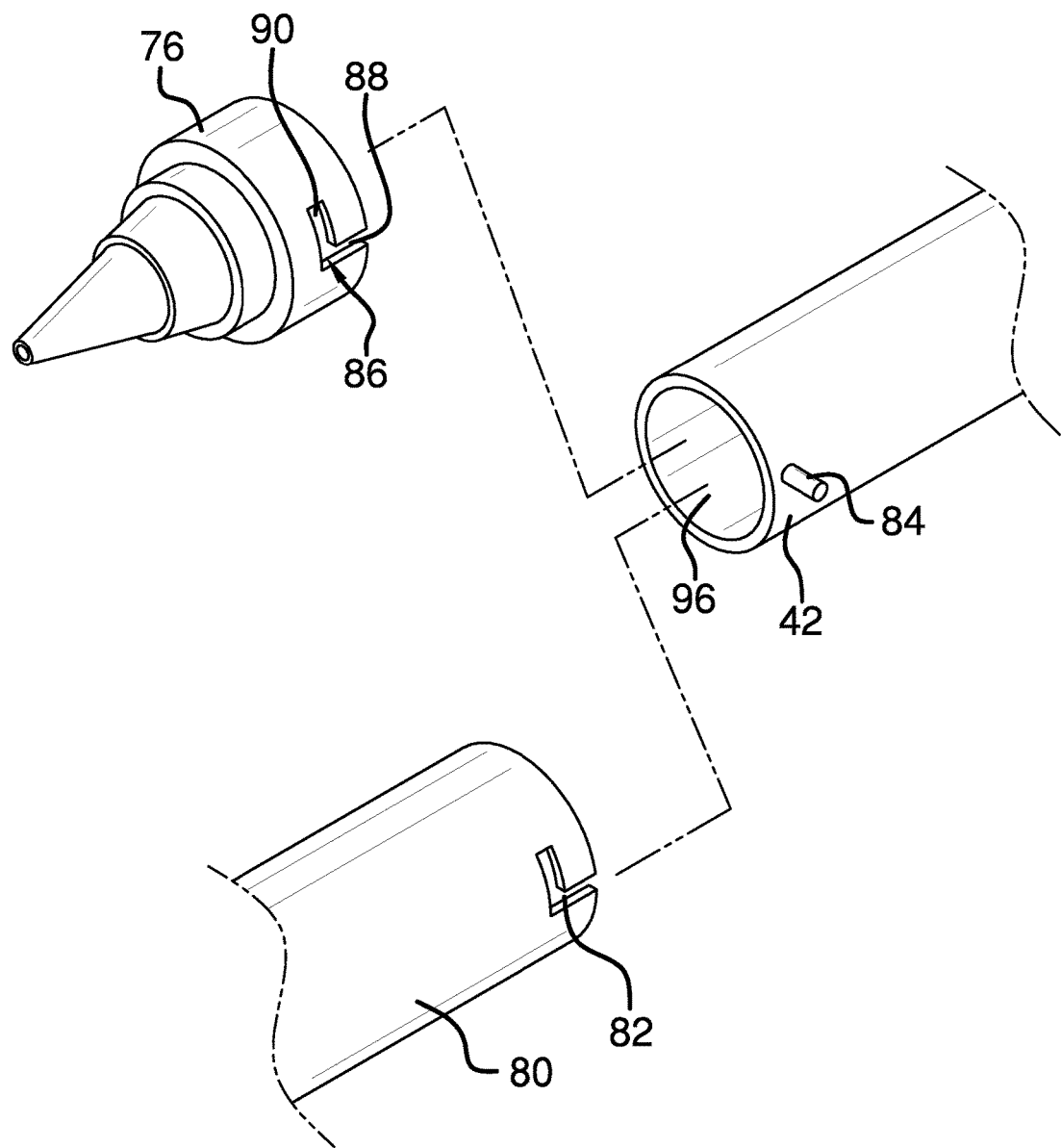
FIG. 8 is a top front side exploded view of alternative connections of a drain of the disclosure.

With reference now to the drawings, and in particular to FIGS. 1 through 8 thereof, a new pan device embodying the principles and concepts of an embodiment of the disclosure and generally designated by the reference numeral 10 will be described.

As best illustrated in FIGS. 1 through 8, the limb irrigation pan device 10 generally comprises a frame 12 having a pair of opposed ends 14 and a pair of longitudinal sides 16 extending between the opposed ends 14. Each of the opposed ends 14 has a respective upper surface 18. The upper surface 18 of each opposed end 14 is concavely arcuate to facilitate positioning of a limb 20 to extend over the frame 12 and between the longitudinal sides 16. The frame 12 may have a length sufficient to accommodate either an arm 22 or a leg 24. This can be achieved with a length between 45 and 65 centimeters. An upper edge 26 of the frame extending fully around the frame 12 and including the upper surface 18 of each opposed end 14 defines an open top 28 of the frame 12. Space between the longitudinal sides 16 may be between 15 and 25 centimeters. A height of the frame 12 may be between 10 and 16 centimeters.

A base 30 is coupled to and extends between the opposed ends 14. The base 30 is further coupled to and extends between the longitudinal sides 16. The base 30 is solid to define a well 32 with the opposed ends 14 and longitudinal sides 16 such that the well 32 is configured for collecting a fluid 34 passed into the frame 12 through the open top 28. A sling 36 is coupled to the frame 12. The sling 36 is porous and may be formed by a flexible sheet of material such as sterile cotton, nylon, or other conventional material suitable for use in a medical setting. The sling 36 is configured for passing the fluid 34 through the sling 36 to be collected in the well 32. Each of a pair of side edges 38 of the sling 36 is coupled to an associated one of the longitudinal sides 16 of the frame 12. The sling 36 and upper surfaces 18 of the opposed ends 14 are sized to substantially align end edges 40 of the sling 36 with the upper surfaces 18. Thus, the sling 36 is configured for supporting the limb 20 over the well 32. The sling 36 may be either constructed of a material which can be cleaned and re-sterilized for repeated use or made to be disposable after a single use.

A drain 42 is coupled to the frame 12. The drain 42 is in fluid communication with the well 32 wherein the drain 42 is configured for draining the fluid 34 from the well 32. The drain 42 may be positioned at an end 44 of the well 32. A nozzle 76 may be detachably coupled to the drain 42. A coupler 46 such as a chain, line, or the like has a first end 48 coupled to the nozzle 76 and a second end 50 coupled to the frame 12 to prevent loss of the nozzle 76. A projection 84 may extend from the drain 42 proximate an open end 96 of the drain 42. The projection 84 may be seated into a slot 86 extending into the nozzle 76 when the nozzle 76 is coupled to the drain 42. The slot 86 may be substantially L-shaped having a first section 88 extending longitudinally along the nozzle 76 and a second section 90 extending transversely from the first section 88. Thus, the projection 84 will prevent the nozzle from being inadvertently disengaged from the drain 42. The nozzle 76 may be used to reduce the circumference of the open end 96 of the drain 42 when needed. The circumference of the open end 96 of the drain 42 may be such that it mates with a suction hose 80 to be used in an existing operating room. The hose 80 may be provided with a slit 82 having similar structure to the slot 86 such that the projection 84 similarly engages the slit 82 in the hose 80. The frame 12, the drain 42, and the nozzle 76 may each be constructed of a durable material suitable for being sterilized between uses.

Each of a pair of end pads 52 is coupled to an associated one of the opposed ends 14 of the frame 12 covering the upper surface 18 of the associated opposed end 14. Each pad 52 is provided to comfortably support the limb 20. Each pad 52 may further comprise a non-absorbent outer surface to facilitate creating a seal between the pad 52 and the limb 20 to inhibit the fluid 34 from spilling over the pad 52. Each of a plurality of sockets 54 extends into the frame 12. Each socket 54 extends into the upper surface 18 of an associated one of the opposed ends 14 of the frame 12. Each of a plurality of projections 56 extends from an associated one of the pads 52. Each projection 56 is received in an associated one of the sockets 54 to removably couple each pad 56 to the frame 12 and inhibit lateral movement of the pad 52 relative to the upper surface 18 of the associated opposed end 14.

Each of a plurality of holes 58 extends through the frame 12. The holes 58 are arranged into two rows 60 of the holes 58. Each row 60 of the holes 58 extends along an associated one of the longitudinal sides 16 of the frame 12. Each row 60 may extend through a lip 78 extending arcuately outwardly and downwardly away from the open top 28. Each of a plurality of disks 62 is coupled to the sling 36. Each disk 62 is received through an associated one of the holes 58 wherein the sling 36 is coupled to the frame 12. Each of a plurality of tethers 64 is coupled to and extends between the sling 36 and an associated one of the disks 62 facilitating insertion of each disk 62 into the associated hole 58. A pair of reinforcing strips 66 may be provided. Each reinforcing strip 66 is coupled to the sling 36 extending along a full length of an associated one of the side edges 38 of the sling 36. The strips 66 may be formed by folding over a section of the sling 36. Each tether 64 extends from an associated one of the reinforcing strips 66.

A bottom surface 68 of the well 32 is sloped towards the drain 42. A drain slot 70 extends through one of the opposed ends 14 of the frame 12. The drain 42 is positioned adjacent to the drain slot 70 and the nozzle 76 extends through the drain slot 70 when the nozzle 76 is coupled to the drain 42. An outer surface 72 of the nozzle 76 may be elongated and grooved wherein the nozzle 76 is graduated and configured for coupling to a tube 74, smaller than the hose 80, such that the tube 74 is in fluid communication with the well 32 whereby the fluid 34 may be drained from the well 32 through the tube 74 to control ultimate collection and disposal of the fluid 34 and debris collected within the well 32.

The device 10 is used when irrigating a wound on the limb 20. The sling 36 is coupled to the frame 12 and the limb 20 is supported on the frame 12 and sling 36 to position the wound over the well 32. The fluid 34 may then be washed over the limb 20 and into the wound to cleanse the wound and remove debris. The fluid 34 drains through the sling 36 and is collected in the well 32 and subsequently drained from the well 32 through the drain 42. Debris passes through the sling 36. Thus, the device 10 facilitates collection of the fluid 34 and debris.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:
1. A limb irrigation pan device comprising:
   a frame having a pair of opposed ends and a pair of longitudinal sides extending between said opposed ends, each of said opposed ends having a respective upper surface, said upper surface of each said opposed end being concavely arcuate, an upper edge of said frame defining an open top of said frame;
   a base coupled to and extending between said opposed ends, said base being coupled to and extending between said longitudinal sides, said base being solid and defining a well such that said well is configured for collecting a fluid passed into said frame through said open top;
   a sling coupled to said frame, said sling being porous wherein said sling is configured for passing the fluid through said sling to be collected in said base;
   a drain coupled to said frame, said drain being in fluid communication with said well wherein said drain is configured for draining the fluid from the well;
   a plurality of holes arranged into a row extending through said frame, said row extending through a lip extending arcuately and downwardly away from the open top of the frame, each of said holes being positioned on an outside of said frame relative to said well; and
   a plurality of disks coupled to said sling, each said disk being received through an associated one of said holes wherein said sling is coupled to said frame.

2. The device of claim 1, further comprising a pair of end pads, each end pad being coupled to an associated one of said opposed ends of said frame, each said pad covering said upper surface of said associated opposed end.

3. The device of claim 2, further comprising each of a pair of side edges of said sling being coupled to an associated one of said longitudinal sides of said frame.

4. The device of claim 1, further comprising said holes being arranged into two rows of holes, each row of holes extending along an associated one of said longitudinal sides of said frame.

5. The device of claim 1, further comprising a plurality of tethers, each tether being coupled to and extending between said sling and an associated one of said disks.

6. The device of claim 5, further comprising a pair of reinforcing strips, each said reinforcing strip being coupled to said sling extending along an associated one of said side edges of said sling.

7. The device of claim 6, further comprising each said tether extending from an associated one of said reinforcing strips.

8. The device of claim 1, further comprising a bottom surface of said well being sloped towards said drain.

9. The device of claim 1, further comprising:
   a drain slot extending through one of said opposed ends of said frame; and
   said drain being positioned at an end of said well, said drain extending through said drain slot.

10. The device of claim 1, further comprising a nozzle detachably coupled to said drain.

11. The device of claim 10, further comprising an outer surface of said nozzle being elongated and graduated wherein said drain is configured for coupling to a tube such that said tube is in fluid communication with said well whereby the fluid is drained from said well through the tube.

12. The device of claim 11, further comprising a coupler having a first end coupled to said nozzle and a second end coupled to said frame.

13. The device of claim 2, further comprising:
- a plurality of sockets extending into said frame, each said socket extending into said upper surface of an associated one of said opposed ends of said frame; and
- a plurality of projections, each projection extending from an associated one of said pads, each projection being received in an associated one of said sockets.

14. A limb irrigation pan device comprising:
- a frame having a pair of opposed ends and a pair of longitudinal sides extending between said opposed ends, each of said opposed ends having a respective upper surface, said upper surface of each said opposed end being concavely arcuate, an upper edge of said frame defining an open top of said frame;
- a base coupled to and extending between said opposed ends, said base being coupled to and extending between said longitudinal sides, said base being solid and defining a well such that said well is configured for collecting a fluid passed into said frame through said open top;
- a sling coupled to said frame, said sling being porous wherein said sling is configured for passing the fluid through said sling to be collected in said base, each of a pair of side edges of said sling being coupled to an associated one of said longitudinal sides of said frame;
- a drain coupled to said frame, said drain being in fluid communication with said well wherein said drain is configured for draining the fluid from the well, said drain being positioned at an end of said well, a nozzle detachably coupled to said drain, an outer surface of said nozzle being elongated and graduated wherein said drain is configured for coupling to a tube such that said tube is in fluid communication with said well whereby the fluid is drained from said well through the tube;
- a coupler having a first end coupled to said nozzle and a second end coupled to said frame; a pair of end pads, each end pad being coupled to an associated one of said opposed ends of said frame, each said pad covering said upper surface of said associated opposed end;
- a plurality of sockets extending into said frame, each said socket extending into said upper surface of an associated one of said opposed ends of said frame;
- a plurality of projections, each projection extending from an associated one of said pads, each projection being received in an associated one of said sockets;
- a plurality of holes arranged into a row extending through said frame, said row extending through a lip extending arcuately and downwardly away from the open top of the frame, each of said holes being positioned on an outside of said frame relative to said well, said holes being arranged into two rows of holes, each row of holes extending along an associated one of said longitudinal sides of said frame and through a lip extending arcuately and downwardly away from the open top of the associated one of said longitudinal sides the frame;
- a plurality of disks coupled to said sling, each said disk being received through an associated one of said holes wherein said sling is coupled to said frame;
- a plurality of tethers, each tether being coupled to and extending between said sling and an associated one of said disks;
- a pair of reinforcing strips, each said reinforcing strip being coupled to said sling extending along an associated one of said side edges of said sling, each said tether extending from an associated one of said reinforcing strips;
- a bottom surface of said well being sloped towards said drain; and
- a drain slot extending through one of said opposed ends of said frame, said drain extending through said drain slot.

\* \* \* \* \*